United States Patent [19]

Sestanj et al.

[11] Patent Number: 4,925,968
[45] Date of Patent: May 15, 1990

[54] N-ACYL-N-NAPHTHOYLGLYCINES AS ALDOSE REDUCTASE INHIBITORS

[75] Inventors: Kazimir Sestanj, Monmouth Junction; Jay E. Wrobel, Lawrenceville; Joseph M. Kelly, Bloomfield, all of N.J.

[73] Assignee: American Home Products Corporation, New York, N.Y.

[21] Appl. No.: 294,712

[22] Filed: Jan. 9, 1989

Related U.S. Application Data

[62] Division of Ser. No. 137,479, Dec. 23, 1987.

[51] Int. Cl.$^5$ .......................................... C07C 175/065
[52] U.S. Cl. ........................................ 560/21; 560/28; 564/44
[58] Field of Search ..................... 560/28, 21; 564/44

[56] References Cited

U.S. PATENT DOCUMENTS

| 4,391,816 | 7/1983 | Sestanj et al. | 514/423 |
| 4,391,825 | 7/1983 | Bellini et al. | 514/562 |
| 4,439,617 | 3/1984 | Sestanj et al. | 560/39 |
| 4,447,452 | 5/1984 | Sestanj | 514/567 |
| 4,568,693 | 2/1986 | Sestanj et al. | 514/524 |
| 4,672,058 | 6/1987 | Bellini et al. | 514/62 |
| 4,672,059 | 6/1987 | Sestanj et al. | 514/62 |
| 4,820,727 | 4/1989 | Wrobel et al. | 514/510 |
| 4,843,062 | 6/1989 | Sestanj et al. | 514/4 |

Primary Examiner—Bruce Gray
Attorney, Agent, or Firm—Walter Patton

[57] ABSTRACT

Disclosed herein are N-acyl-N-naphthoylglycines and methods of their preparation. The N-acyl-N-naphthoylglycines are novel aldose reductase inhibitors useful for the treatment or prevention of diabetic complications.

1 Claim, No Drawings

N-ACYL-N-NAPHTHOYLGLYCINES AS ALDOSE REDUCTASE INHIBITORS

This is a divisional application of copending U.S. Ser. No. 137,479, filed December 23, 1987.

BACKGROUND OF THE INVENTION

This invention relates to N-acyl-N-naphthoylglycines, to the processes for their preparation, to methods for using the compounds, and to pharmaceutical preparations thereof. The compounds have pharmaceutical properties which render them beneficial for the treatment of diabetes mellitus and associated conditions.

For many years diabetes mellitus has been treated with two established types of drugs, namely insulin and oral hypoglycemic agents. These drugs have benefited hundreds of thousands of diabetics by improving their well-being and prolonging their lives. However, the resulting longevity of diabetic patients has led to complications such as neuropathy, nephropathy, retinopathy, cataracts and atherosclerosis. These complications have been linked to the undesirable accumulation of sorbitol in diabetic tissue, which in turn resulted from the high levels of glucose characteristic of the diabetic patient.

In mammals, including humans, the key enzyme involved in the conversion of hexoses to polyols (e.g. the sorbitol pathway) is aldose reductase. J. H. Kinoshita and collaborators, see J. H. Kinoshita et al, Biochem. Biophys. Acta, 158,472 (1968) and references cited therein, have demonstrated that aldose reductase plays a central role in the etiology of galactosemic cataracts by effecting the conversion of galactose to dulcitol (galactitol) and that an agent capable of inhibiting aldose reductase can prevent the detrimental accumulation of dulcitol in the lens. Furthermore, a relationship between elevated levels of glucose and an undesireable accumulation of sorbitol has been demonstrated in the lens, peripheral nervous cord and kidney of diabetic animals, see A. Pirie and R. van Heyningen, Exp. Eye Res., 3,124 (1964); L. T. Chylack and J. H. Kinoshita, Invest. Ophthal., 8,401 (1969) and J. D. Ward and R. W. R. Baker, Diabetol., 6,531 (1970).

K. Sestanj et al, U.S. Pat. No. 4,568,693, February 4, 1986, disloses N-naphthoylglycine derivatives having aldose reductase activity. The compounds of the present invention have an acyl substituent on the glycine nitrogen. Still other related compounds having a similar utility are N-naphthoylglycine derivatives of K. Sestanj et al, U.S. Pat. No. 4,439,617, March 27, 1984; N-(naphthalenylthioxomethyl)amino acid derivatives of K. Sestanj et al, U.S. Pat. No. 4,391,816, July 5, 1983; N-[(2-naphthalenyl)thioxomethyl]glycine derivatives of K. Sestanj, U.S. Pat. No. 4,447,452, May 8, 1984; and N-[[6-(lower alkoxy)-5-(trifluoromethylthio)-1-naphthalenyl]thioxomethyl]-N-(lower alkyl)glycines of F. Bellini et al, U.S. Pat. No. 4,391,825, July 5, 1983. Accordingly, these compounds represent an important new approach for the treatment of diabetes mellitus.

Y. Mitin et al, Izv. Akad. Nauk SSSR, Ser. Khim. 11, 2666 (1968) (C.A. 70:68721 m) discloses N,N-dibenzoylglycine as a chemical intermediate without disclosing any biological activity.

A. J. Bates et al, Helv. Chim. Acta, 58 (3) 688 (1975) discloses N,N[1]-bis(benzyloxycarbonyl)glycylglycine as a chemical intermediate without disclosing any biological activity.

SUMMARY OF THE INVENTION

The N-acyl-N-naphthoylglycines of this invention are represented by formula (I)

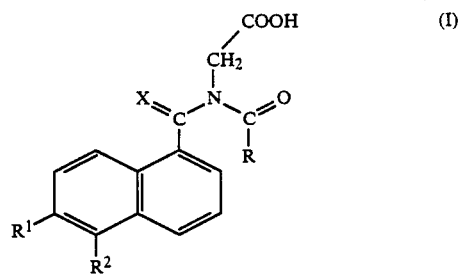

wherein R is hydrogen, lower alkyl containing 1 to 3 carbon atoms, lower alkoxy containing 1 to 6 carbon atoms, trifluoroethoxy, phenyl, benzyloxy, substituted benzyloxy, or lower dialkylamino containing 1 to 3 carbon atoms; $R^1$ is hydrogen or lower alkoxy containing 1 to 3 carbon atoms; $R^2$ is halogen or lower perfluoroalkyl containing 1 to 3 carbon atoms; X is oxygen or sulfur, and the pharmaceutically acceptable salts thereof.

Preferred compounds of the present invention are represented by formula (II)

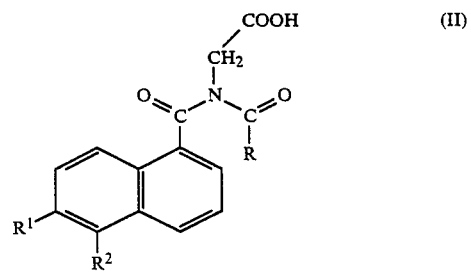

wherein R is hydrogen, lower alkyl containing 1 to 3 carbon atoms, lower alkoxy containing 1 to 6 carbon atoms, trifluoroethoxy, phenyl, benzyloxy, substituted benzyloxy, or lower dialkylamino containing 1 to 3 carbon atoms; $R^1$ is hydrogen or lower alkoxy containing 1 to 3 carbon atoms; $R^2$ is halogen or lower perfluoroalkyl containing 1 to 3 carbon atoms, and the pharmaceutically acceptable salts thereof.

Still further preferred compounds of the present invention are represented by formula (III)

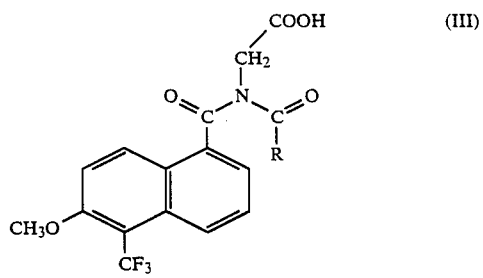

wherein R is hydrogen or alkoxy wherein alkoxy contains 1 to 6 carbon atoms, and the pharmaceutically acceptable salts thereof.

The most preferred compounds of the present invention are designated:

N-(ethoxycarbonyl)-N-[[6-methoxy-5-(trifluoromethyl)-1-naphthalenyl]carbonyl]glycine;
N-(methoxycarbonyl)-N-[[6-methoxy-5-(trifluoromethyl)-1-naphthalenyl]carbonyl]glycine; and
N-formyl-N-[[6-methoxy-5-(trifluoromethyl)-1-naphthalenyl]carbonyl]glycine; and the pharmaceutically acceptable salts thereof.

Also included in the present invention are the chemical intermediate compounds of formula (VII)

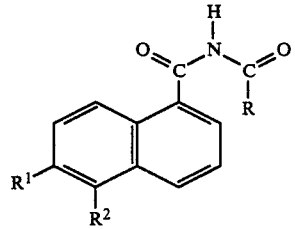

wherein R, R$^1$, and R$^2$ are as defined above.

The N-acyl-N-naphthoylglycines of the present invention can be prepared by the processes described hereinafter.

A method is provided for preventing or relieving diabetes mellitus associated complications in a diabetic mammal by administering to said mammal a prophylactic or alleviating amount of a compound of formulas (I), (II), or (III). Such complications include neuropathy, nephropathy, retinopathy and cataracts.

The compounds of formulas (I), (II), or (III), when admixed with a pharmaceutically acceptable carrier, form a pharmaceutical composition which can be used according to the preceding method.

DETAILED DESCRIPTION OF THE INVENTION

The compounds of this invention, represented by formulas (I), (II), and (III), can exist in rotameric forms. More explicitly, mesomerism imparts a partial double bond character to the carbonyl-nitrogen bonds. This partial double bond character leads to restricted rotation about the carbonyl-nitrogen bonds giving rise to cis and trans rotamers, the restricted rotation being augmented by the bulkiness of neighboring groups. The rotameric forms represented by structural formulas (I$^1$), (I$^2$), (I$^3$), and (I$^4$) are included within the scope of this invention:

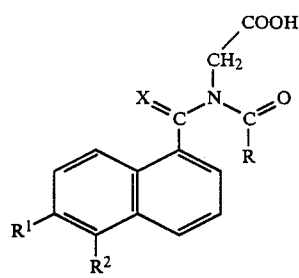

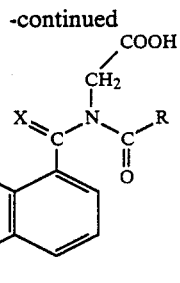

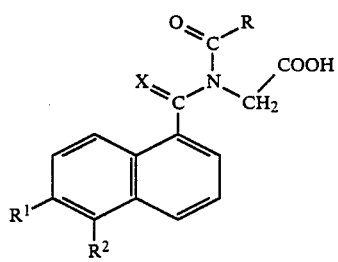

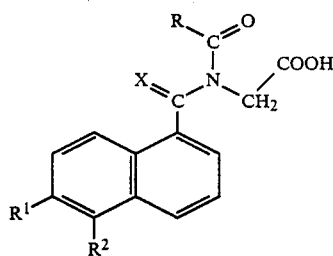

wherein R, R$^1$, R$^2$, and X are as defined above.

For brevity, the compounds of this invention, including their rotameric forms, are referred to herein as compounds of formula (I), (II), and (III).

The compounds of formula (I) form salts with suitable therapeutically acceptable inorganic and organic bases. These derived salts posses the same activity as their parent acid and are included within the scope of this invention. The acid is transformed in excellent yield into the corresponding therapeutically acceptable salt by neutralization of said acid with the appropriate inorganic or organic base. The salts are administered usually in the same manner as the parent acid compounds. Suitable inorganic bases to form these salts include, for example, the hydroxides, carbonates or bicarbonates of the therapeutically acceptable alkali metals or alkaline earth metals, for example, sodium, potassium, magnesium, calcium and the like. Suitable organic bases include the following amines: benzylamine; lower mono-, di- and trialkylamines, the alkyl radicals of which contain up to three carbon atoms, such as methylamine, dimethylamine, trimethylamine, ethylamine, di- and triethylamine, methylethylamine, and the like; mono-, di- and trialkanolamines, the alkanol radicals of which contain up to three carbon atoms, for example, mono-, di- and triethanoamine; alkylene-diamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxyalkyl derivatives, such as N-methyl-morpholine and N-(2-hydroxyethyl)-piperidine, as well as pyrdine. Furthermore, there may be mentioned the corresponding quaternary salts, such as the tetraalkyl (for example tetramethyl), alkyl-alkanol (for example methyl-triethyl and trimethyl-monoethanol) and cyclic ammonium salts, for example the N-methylpyridinium, N-methyl-N-(2-hydroxyethyl)morpholinium, N,N-dimethylmorpholinium, N-methyl-N-(2-hydroxyethyl)-morpholinium, N,N-dimethylpiperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula (I) in water containing at least one equivalent amount of a hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acidic compound of formula (I) is dissolved in a suitable solvent of either moderate or low polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of lower polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula (I) with an equivalent amount of the corresponding quaternary ammonium hydroxide in water solution, followed by evaporation of the water.

The N-acyl-N-naphthoylglycines of this invention may be administered to mammals, for example, man, monkeys or dogs, either alone or in dosage forms, i.e., capsules or tablets, combined with pharmacologically acceptable excipients.

Advantageously the compounds of this invention may be given orally. However, the method of administering the present active ingredients of this invention is not to be construed as limited to a particular mode of administration. For example, the compounds may be administered topically directly to the eye in the form of drops of sterile, buffered ophthalmic solutions, preferably of pH 7.2-7.6. Also, they may be administered orally in solid form containing such excipients as starch, milk sugar, certain types of clay and so forth. They may also be administered orally in the form of solutions or they may be injected parenterally. For parenteral administration they may be used in the form of a sterile solution, preferably of pH 7.2-7.6, containing a pharmaceutically acceptable buffer.

The dosage of the N-acyl-N-naphthoylglycines will vary with the form of administration. Furthermore, it will vary with the particular host under treatment. Generally, treatment is initiated with small dosages substantially less than the optimal dose of the compound. In general, the compounds of this invention are most desirably administered at a concentration level that will generally afford effective results without causing any harmful or deleterious side effects. For topical administration, a 0.05-1.8% solution may be administered dropwise in the eye. The frequency of instillation varies with the subject under treatment from a drop every two or three days to once daily. For oral or parenteral administration a preferred level of dosage ranges from about 0.5 mg to about 1000 mg per kilo of body weight per day, although aforementioned variations will occur. However, a dosage level that is in the range of from about 5.0 mg to about 60 mg per kilo of body weight per day is most satisfactory.

Unit dosage forms such as capsules, tablets, pills and the like may contain from about 25 mg to about 1250 mg of the active ingredients of this invention with a pharmaceutical carrier. Thus, for oral administration, capsules can contain from between about 25 mg to about 1250 mg of the active ingredients of this invention with or without a pharmaceutical diluent. Tablets, either effervescent or noneffervescent, can contain between about 25 to 1250 mg of the active ingredients of this invention together with conventional pharmaceutical carriers. Thus, tablets, which may be coated and either effervescent or noneffervescent, may be prepared according to the known art. Inert diluents or carriers, for example, magnesium carbonate or lactose, can be used together with conventioal disintegrating agents for example, magnesium stearate.

The N-acyl-N-naphthoylglycines can also be used in combination with insulin or oral hypoglycemic agents to produce a beneficial effect in the treatment of diabetes mellitus. In this instance, commercially available insulin preparations or oral hypoglycemic agents, exemplified by acetohexamide, chlorpropamide, tolazamide, tolbutamide and phenformin, are suitable. The compounds hereof can be administered sequentially or simultaneously with insulin or the oral hypoglycemic agent. Suitable methods of administration, compositions and doses of the insulin preparation or oral hypoglycemic agent are described in medical textbooks; for instance, "Physicians' Desk Reference", 36 ed., Medical Economics Co., Oradell, N.J. U.S.A., 1982. When used in combination, the N-acyl-N-naphthoylglycines are administered as described previously. The N-acyl-N-naphthoylglycines can be administered with the oral hypoglycemic agent in the form of a pharmaceutical composition comprising effective amounts of each agent.

The aldose reductase inhibiting property of the compounds of this invention and the utilization of the compounds in preventing, diminishing and alleviating diabetic complications are demonstrable in experiments using galactosemic rats, see Dvornik et al, Science, 182, 1146 (1973). Such experiments are exemplified hereinbelow after the listing of the following general comments pertaining to these experiments:

(a) Four or more groups of six male rats, 50-70 g, Sprague-Dawley strain, were used. The first group, the control group, was fed a mixture of laboratory chow (rodent Laboratory Chow, Purina) and glucose at 20% (w/w %) concentration. The untreated galactosemic group and the drug-treated groups were fed a similar diet in which galactose is substituted for glucose. The test compound was either admixed to the diet or administered by gavage. In experiments involving compound administration in the diet, the average dose administered was calculated from the actual food intake of the animals in each group. The concentration of galactose in the diet of the treated groups was the same as that for the untreated galactosemic group.

(b) After four days, the animals were killed by decapitation. The eyeballs were removed and punctured with a razor blade; the freed lenses were rolled gently on filter paper and weighed. The sciatic nerves were dissected as completely as possible and weighed. Both tissues when frozen can be kept up to two weeks before being analyzed for galactitol.

(c) The polyol determination was performed by a modification of the procedure of M. Kraml and L. Cosyns, Clin. Biochem., 2,373 (1969). Only two minor reagent changes were made: (a) The rinsing mixture was an aqueous 5% (w/v) trichloroacetic acid solution and (b) the stock solution was prepared by dissolving 25 mg of dulcitol in 100 mL of an aqueous trichloroacetic acid solution. [N.B.: For each experiment the average value found in the tissue from rats fed the glucose diet was subtracted from the individual values found in the corresponding tissue in galactose-fed rats to obtain the amount of polyol accumulated.] The aldose reductase inhibiting effects of the compounds of formula (I) were also tested by employing an in vitro testing procedure similar to that described by S. Hayman and J. H. Kinoshita, J. Biol. Chem., 240, 877 (1965). In the present case the procedure of Hayman and Kinoshita was modified in that the final chromatography step was omitted in the preparation of the enzyme from bovine lens.

The following tabulated results show that the N-acyl-N-naphthoylglycines of this invention show the property that they diminish the accumulation of galactitol in the lenses and sciatic nerves of rats fed galactose. The figures under L, N, and D represent the percentage decrease of galactitol accumulation in the tissues of the lens, sciatic nerve, and diaphragm, respectively, for treated rats as compared to untreated rats.

Examination of the results tabulated below show that the N-acyl-N-naphthoylglycines of this invention are well suited as aldose reductase inhibitors. For example, N-(ethoxycarbonyl)-N-[[6-methoxy-5-(trifluoromethyl)-1-naphthalenyl]carbonyl]glycine at a dose of 57 mg/kg/day and N-(methoxycarbonyl)-N-[[6-methoxy-5-(trifluoromethyl)-1-naphthalenyl]carbonyl]glyine at a dose of 48 mg/kg/day give comparable results to N-[[6-methoxy-5-(trifluoromethyl)-1-naphthalenyl]thioxomethyl]-N-methylglycine at 9 mg/kg/day. The latter compound, is also known as tolrestat.

| Ex. | R | % Inhibition IN VITRO | | | % Lowering dulcitol accumulation IN VIVO | | | | Synthetic Process (Scheme) | m.p. °C. |
|---|---|---|---|---|---|---|---|---|---|---|
| | | $10^{-5}$ M | $10^{-6}$ M | $10^{-7}$ M | mg/kg | (%)L | (%)N | (%)D | | |
| 1 | —O—CH$_2$—CH$_3$ | 97 | 94 | 47 | 97 | 12 | 90 | 83 | 2 | 86–88.5 |
| | | | | | 57 | 19 | 56 | 70 | | |
| 2 | —O—CH$_3$ | 98 | 97 | 82 | 48 | N.S. | 70 | 54 | 1 | 148–150 |
| 3 | —O—CH$_2$—CH$_2$—CH$_3$ | 95 | 90 | 81 | 48 | N.S. | N.S. | N.S. | 1 | 101–102 |
| | | | 48% (4 × $10^{-8}$ M) | | | | | | | |
| 4 | —O—CH(CH$_3$)$_2$ | 96 | 86 | 35 | N.S. | N.S. | N.S. | N.S. | 1 | 138–140 |
| 5 | —O—CH$_2$—C(CH$_3$)$_3$ | 90 | 64 | 18 | 105 | N.S. | N.S. | N.S. | 1 | 118–120 |
| 6 | —O—CH$_2$—C$_6$H$_5$ | 95 | 89 | 66 | 67 | N.S. | N.S. | N.S. | 1 | 158–160 |
| 7 | —O—CH$_2$—C$_6$H$_3$(Cl)(NO$_2$) | 95 | 89 | 49 | 107 | N.S. | N.S. | N.S. | 1 | 187–189 |
| 8 | —H | 95 | 96 | 89 | 107 | 13 | 51 | 82 | 3 | 142–144 |
| 9 | —CH$_3$ | 96 | 91 | 61 | 100 | N.S. | 36 | 39 | 3 | 141–142 |
| 10 | —C$_6$H$_5$ | 90 | 62 | 15 | 50 | N.S. | N.S. | N.S. | 4 | 143–145(dec.) |
| 11 | —N(CH$_3$)$_2$ | 22 | 3 | N.S. | N.D. | — | — | — | 5 | 145–147 |

Core structure (III): naphthalene with CH$_3$O— and —CF$_3$ substituents, bearing an N(CH$_2$COOH) group flanked by two C=O groups, one attached to R.

-continued

| Ex. | R | % Inhibition IN VITRO | | | % Lowering dulcitol accumulation IN VIVO | | | | Synthetic Process (Scheme) | m.p. °C. |
|---|---|---|---|---|---|---|---|---|---|---|
| | | $10^{-5}$ M | $10^{-6}$ M | $10^{-7}$ M | mg/kg | (%)L | (%)N | (%)D | | |

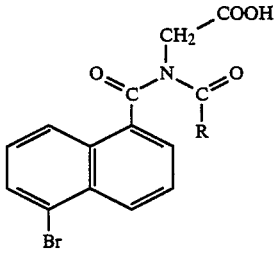

| 12 | —O—CH$_3$ | 85 | 54 | 10 | 102 | N.S. | N.S. | 24 | 1 | 119–121 |
| 13 | —O—CH$_2$—C$_6$H$_5$ | 87 | 57 | 12 | N.D. | — | — | — | 1 | 135–137 |
| 14 | —H | 90 | 73 | 22 | 104 | N.S. | N.S. | 17 | 3 | 167–169 |
| 15 | —CH$_3$ | 82 | 41 | 7 | 112 | N.S. | N.S. | N.S. | 3 | 124–127 |
| 16 | —C$_6$H$_5$ | 83 | 58 | 10 | 111 | N.S. | N.S. | N.S. | 4 | 160–162(dec.) |
| 17 | —N(CH$_3$)$_2$ | 23 | 4 | N.S. | N.D. | — | — | — | 5 | 138–139 |

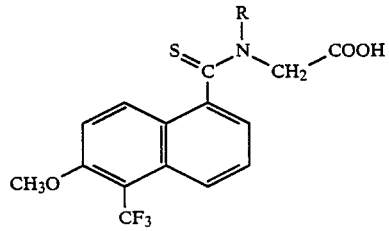

| 18a | —COOCH$_3$ | 94 | 88 | 29 | 51 | N.S. | N.S. | 80 | 6 | 160 |
| 18b | —CH$_3$ (tolrestat) | 98 | 94 | 65 | 9 | N.S. | 58 | 87 | | |

N.S. = not significant
N.D. = not determined
L = lens
N = nerve
D = diaphragm

THE PROCESS

The N-acyl-N-naphthoylglycines can be prepared by the following reaction schemes:

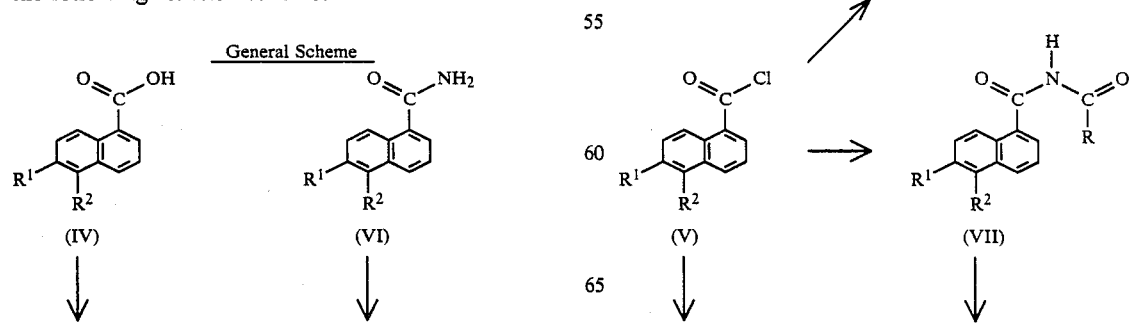

-continued
General Scheme

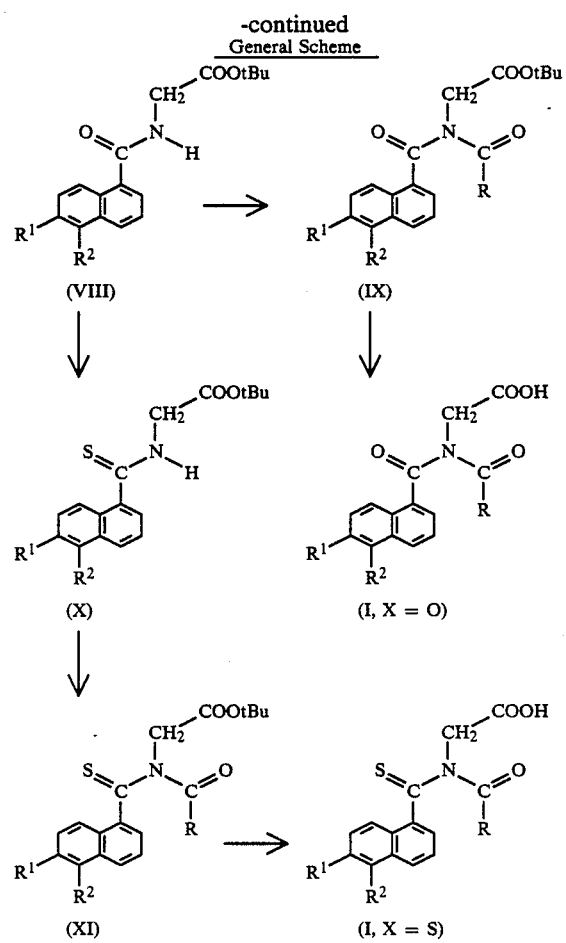

wherein R, $R^1$, and $R^2$ are as defined above.

Referring to the General Scheme, the carboxylic acid (IV), obtained by the process of U.S. Pat. No. 4,568,693 or W. F. Short et al, J. Chem. Soc., 990 (1950), is converted to the corresponding carboxylic acid chloride (V) by reaction with thionyl chloride (1 to 5 eq) in a solvent such as dichloromethane, acetonitrile, chloroform, benzene, or toluene; or thionyl chloride can be used as solvent. A catalytic amount of dimethylformamide is used (0.01 to 0.03 eq). A reaction temperature ranging from 20° C. to 110° C. is used for reaction times ranging from 10 minutes to 3 hours. Other reagents that can be used under similar conditions are phosphorus trichloride and oxalyl chloride.

The carboxylic acid chloride (V) is converted to the corresponding carboxylic acid amide (VI) by reaction of a solution of (V) in an inert organic solvent such as THF, dichloromethane, benzene, or toluene with concentrated aqueous ammonium hydroxide at temperatures ranging from 0° C. to 25° C. for reaction times ranging from 5 minutes to 1 hour.

The corresponding carboxylic acid amide (VI) can alternatively be formed by reacting (V) with a saturated solution of ammonia gas in an inert solvent (such as THF) at temperatures ranging from 0° C. to 25° C. for reaction times ranging from 5 minutes to 1 hour.

According to the procedure of Y. Lin et al, Synthesis, 119 (1980) the carboxylic acid amide (VI) is reacted neat with the appropriate N,N-dimethylcarboxamide dimethylacetal (1 to 5 eq, dimethylformamide dimethylacetal to produce the compounds (VII) wherein R is hydrogen and dimethylacetamide dimethylacetal to produce the compounds (VII) wherein R is methyl) at temperatures of 100° C. to 140° C. for 5 to 25 minutes to produce the appropriate nonisolated amidine. The resulting amidine is added to 50 to 80% aqueous acetic or formic acid at temperatures ranging from 20° C. to 40° C. for 5 to 20 minutes.

Alternatively (VI) is reacted with the appropriate acid anhydride with a catalytic amount of concentrated sulfuric acid (0.05 to 0.2 eq) at temperatures ranging from 80° C. to 120° C. for 30 minutes to 4 hours. For example, reaction of (VI) with 1 to 2 eq acetic anhydride produces (VII) wherein R is methyl.

Reaction of (VI) with a base (sodium hydride, potassium hydride, lithium diisopropylamide, 1.0 to 1.5 eq) in anhydrous THF at temperatures ranging from 0° C. to 30° C. for 20 minutes to 1 hour, and then reaction with N,N-dimethylcarbamoyl chloride (1.0 to 1.2 eq) at temperatures ranging from 20° C. to 65° C. for 1 to 4 hours produces compound (VII) wherein R is $-N(CH_3)_2$.

According to the procedure of C. L. Arcus et al, J. Chem. Soc., 4018 (1954) and 1091 (1957), reaction of (V) with silvercyanate (1 to 2 eq) in an inert organic solvent such as carbon tetrachloride, chloroform, dichloromethane, or benzene at temperatures ranging from 60° C. to 100° C. for reaction times from 1 hour to 24 hours produces the intermediate, nonisolated isocyanate

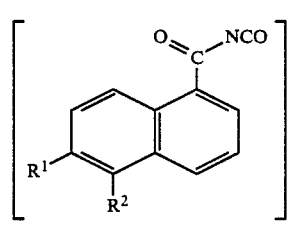

This isocyanate is reacted with the appropriate alcohol (1 to 5 eq) at temperatures ranging from 40° C. to 90° C. for times ranging from 1 to 3 hours to produce the compounds (VII) wherein R is lower alkoxy containing 1 to 6 carbon atoms, trifluoroethoxy, benzyloxy, or substituted benzyloxy.

Benzamide (1.0 to 1.5 eq) is reacted with a base such as sodium hydride, potassium hydride, lithium diisopropylamide (1.1 to 1.6 eq) in anhydrous THF at 0° C. to 30° C. for 20 minutes to 1 hour. The acid chloride (V) is then added and reaction at 20° C. to 65° C. for 1 hour to 4 hours produces the compounds (VII) wherein R is phenyl.

Reaction of (VII) in THF or DMF with 1.0 to 1.3 eq of a base such as sodium hydride, potassium hydride, lithium diisopropylamide (in THF) at temperatures between 0° C. and 60° C. from 10 minutes to 4 hours and then reaction with tert-butyl bromoacetate or tert-butyl chloroacetate (1.0 to 2.0 eq) at temperatures from 0° C. to 65° C. for a period of 30 minutes to 3 days produces the compounds (IX).

Alternatively the carboxylic acid chloride (V) is added to a solution of tert-butyl glycinate (1.0 to 3.0 eq) in an organic solvent such as THF and a base such as triethylamine, potassium carbonate, or sodium bicarbonate and reacted at a temperature of 0° C. to 80° C. for 2 to 24 hours to produce the compounds (VIII).

Reaction of (VIII) with phosphorus pentasulfide (2.0 to 5.0 eq) in an inert solvent toluene or xylene at 80° C.

to 150° C. for 20 minutes to 7 hours or with Lawesson's reagent (0.6 to 3 eq) in the inert solvent toluene or xylene, at 20° C. to 150° C. for 20 minutes to 16 hours produces the compounds (X).

A base, such as solid sodium hydroxide or solid potassium hydroxide (1.0 to 2.0 eq), is added to an acetone solution of (VIII) or (X) at −40° C. and stirred for 30 minutes to 1 hour. To this is added an alkyl chloroformate such as methyl chloroformate or ethyl chloroformate (1.0 to 2.0 eq) and the reaction temperature maintained at 20° C. to 30° C. for 1 hour to 4 hours to produce the compounds (IX) or (XI), respectively.

(IX) or (XI) is reacted with an organic protic acid such as trifluoroacetic acid (1 eq up to use as solvent) or formic acid (5 eq up to use as solvent). The trifluoroacetic acid or formic acid is used as the solvent or the reaction is carried out in a halocarbon solvent, such as dichloromethane, chloroform, or carbon tetrachloride at temperatures from 20° C. to 40° C. for periods of 1 hour to 3 hours to produce the compounds (I, X=O) or (I, X=S), respectively.

Trimethylsilyliodide (1 to 10 eq) in a halocarbon solvent at temperatures from 20° C. to 40° C. for periods of 1 to 3 hours was also used to remove the protective group and produce the compounds (I, X=O) or (I, X=S), respectively.

Preferably, the compounds of the present invention are produced according to the following Schemes:

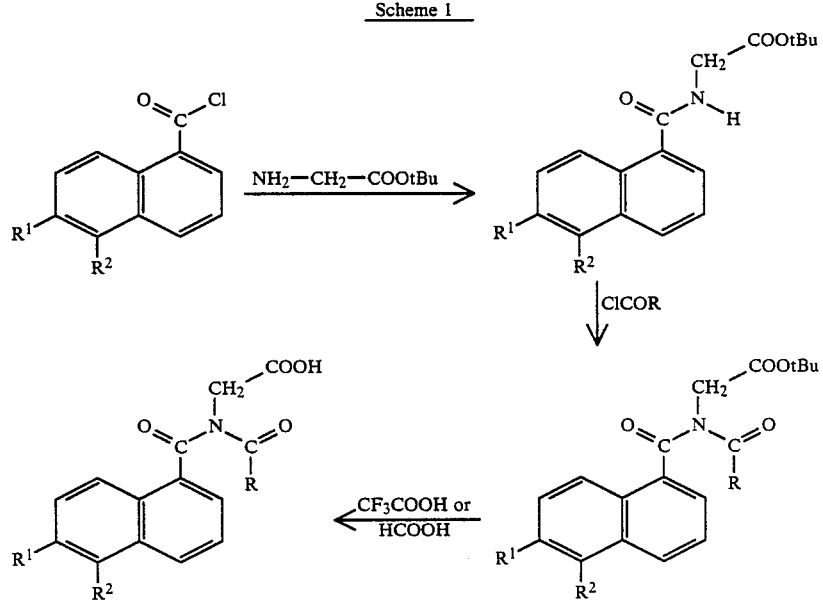

Scheme 1

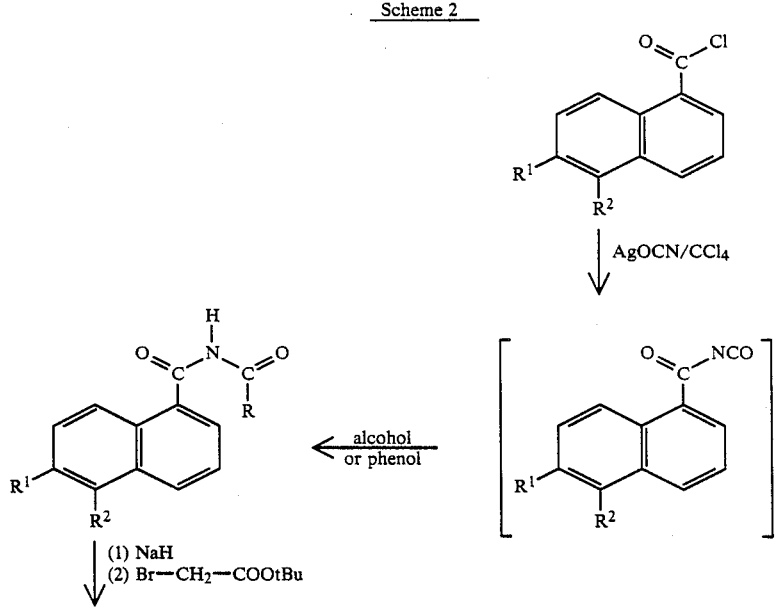

Scheme 2

Scheme 2
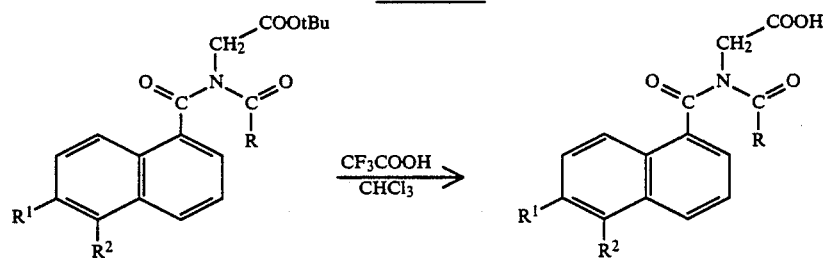
wherein R is alkoxy, aralkoxy, or aryloxy; $R^1$ and $R^2$ are as defined above.
Scheme 3
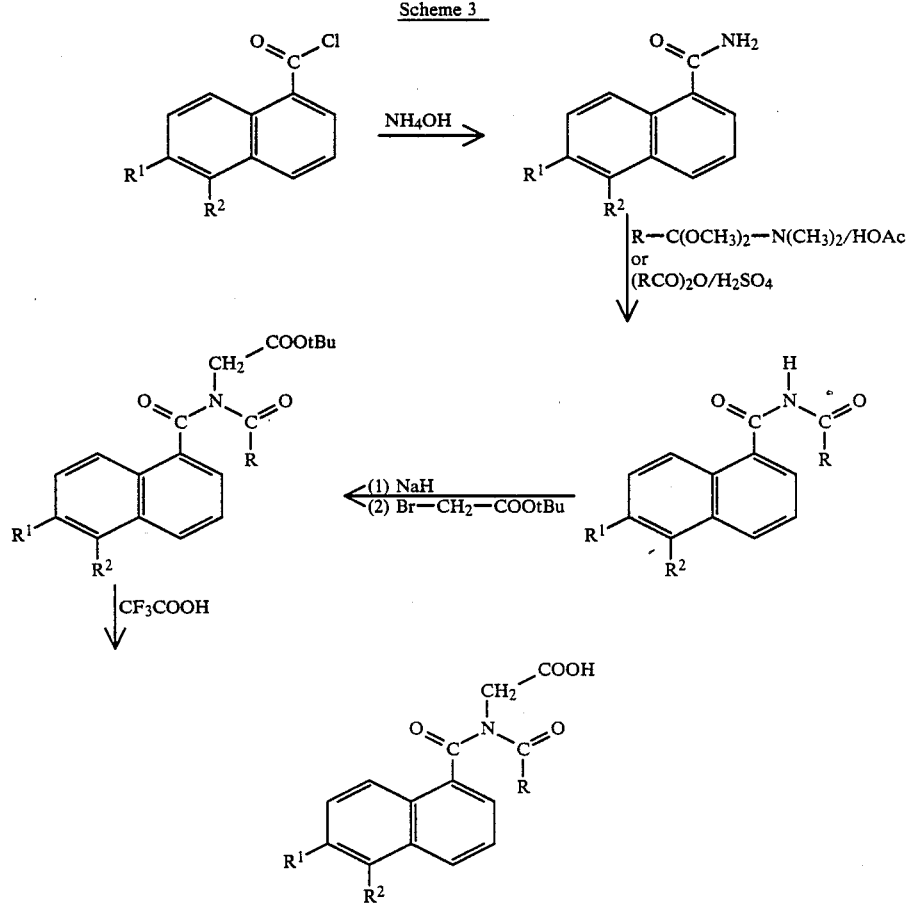
Scheme 4
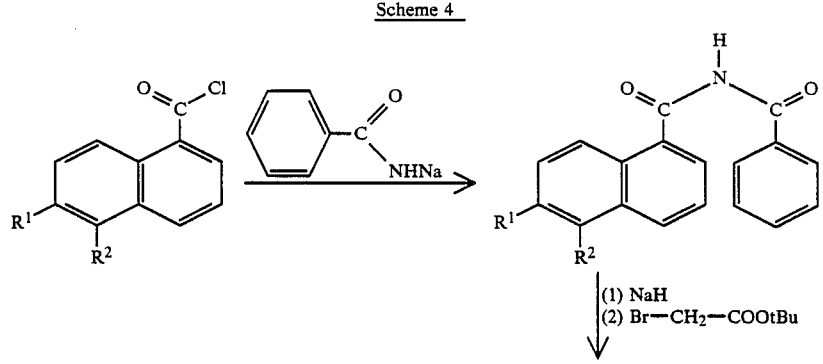

Scheme 4
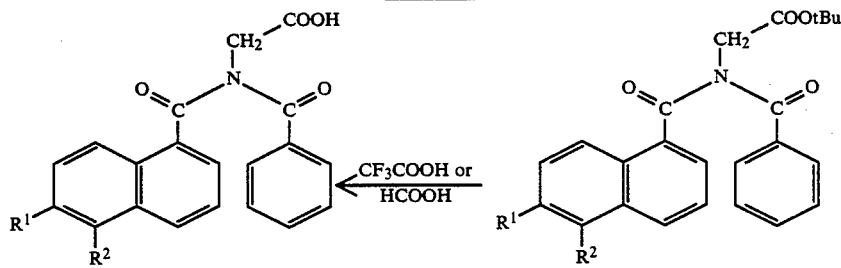
Scheme 5
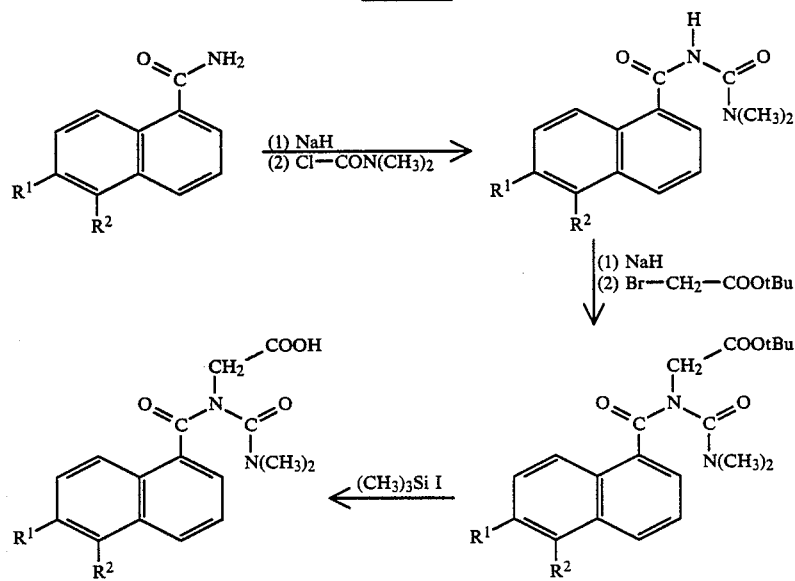
Scheme 6
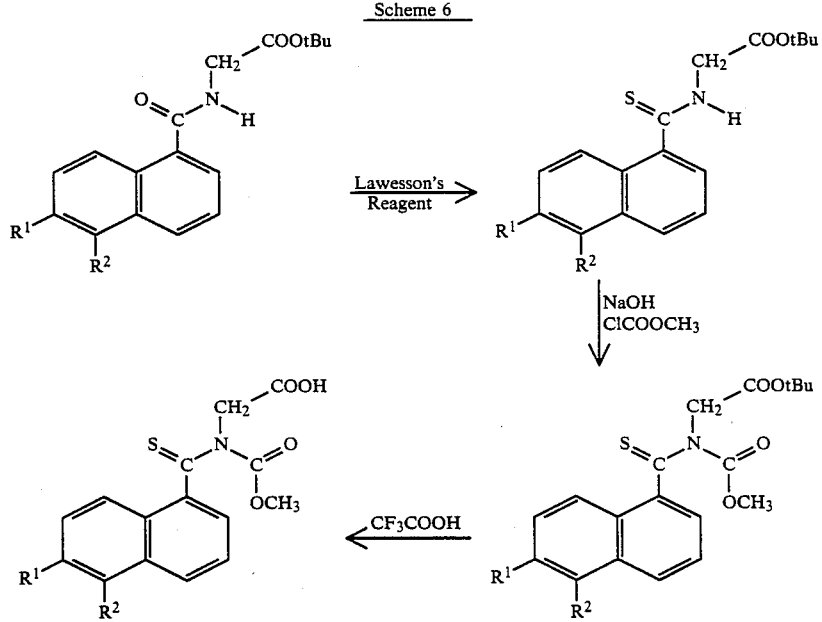
The following Examples further illustrate this invention.

N-[[6-Methoxy-5-(trifluoromethyl)-1-naphthalenyl]carbonyl]-N-[(ethoxy)carbonyl]glycine

[(I): R=OC$_2$H$_5$; R$^1$=OCH$_3$; R$^2$=CF$_3$; X=O]

Step 1. Preparation of N-[[6-methoxy-5-(trifluoromethyl)-1-naphthalenyl]-carbonyl]glycine, 1,1-dimethylethyl ester According to the procedure of C. L. Arcus et al, J. Chem. Soc., 1954, 4018; J. Chem. Soc., 1957, 1091, dimethylformamide (1.0 mL) was added to a solution of 5-(trifluoromethyl)-6-methoxy-1-naphthalenecarboxylic acid, prepared by the process of U.S. Pat. No. 4,568,693 (10.0 g, 37.0 mmol) in thionyl chloride (200 mL) at 20° C. The mixture was refluxed for 4 hours, cooled, solvent evaporated and the residual volatiles purged with benzene. The residual acid chloride was added to a solution of tert-butyl glycinate (8.0 mL) in anhydrous tetrahydrofuran (300 mL), followed by triethylamine (10.0 mL, 136 mmol). The resultant solution was stirred at 20° C. for 24 hours. The solvent was evaporated, the residual oil extracted with ether (500 mL), washed with water (300 mL), saturated sodium bicarbonate (300 mL), and brine (300 mL), dried (MgSO$_4$), filtered, and evaporated to give an oil, which was chromatographed in 15% ethyl acetatehexanes to yield the product (10.1 g, 71.6%), m.p. 104°–106° C.

NMR (DMSO-d$_6$): δ9.0 (s, 1H, NH), 8.58 (d, 1H, ArH), 8.18 (d, 1H, ArH), 7.60–7.80 (m, 3H, ArH), 4.0 (s, 3H, OCH$_3$), 3.95 (d, 2H, NCH$_2$), 1.42 (s, 9H, C(CH$_3$)$_3$).

IR (KBr, cm$^{-1}$): 3310 (N-H), 3000 (C-H), 1760 (C=O), 1740 (C=O), 1620, 1600 (C=C).

Calcd.: C, 59.50; H, 5.25; N, 3.60%.

Found: C, 58.92; H, 5.48; N, 4.02%.

Step 2. Preparation of N-[[6-methoxy-5-(trifluoromethyl)-1-naphthalenyl]-carbonyl]-N-[(ethoxy)carbonyl]glycine, 1,1-dimethylethyl ester According to the procedure of W. Walter et al, Phosphorus Sulfur Relat. Elem., 25(1) 63 (1985) solid sodium hydroxide (powdered, 0.87 g, 21.8 mmol) was added to a solution of N-[[6-methoxy-5-(trifluoromethyl)-1-naphthalenyl]-carbonyl]glycine, 1,1-dimethylethyl ester (5.0 g, 13.0 mmol) in dry acetone (200 mL) at −40° C. then stirred for 30 minutes at −40° C. Ethyl chloroformate (1.5 mL, 15.7 mmol) was added, and the solution allowed to warm to 20° C. over 2 hours. The acetone was evaporated under reduced pressure, water (300 mL) was added, and the precipitated yellow solid was filtered, washed with water (200 mL) and petroleum ether (2×50 mL) then dried at 60° C./0.1 m.m. Hg to yield the pure product (3.1 g, 55.3%), m.p. 105°–106° C.

NMR (CDCl$_3$): δ8.30 (d, 1H, ArH), 7.40–7.60 (m, 4H, ArH), 5.10 (s, 2H, NCH$_2$), 4.0 (s, 3H, OCH$_3$), 3.80 (q, 2H, CH$_2$CH$_3$), 1.50 (s, 9H, C(CH$_3$)$_3$), 0.60 (t, 3H, CH$_2$CH$_3$).

IR (KBr, cm$^{-1}$): 3000 (C-H), 1770, 1740, 1650 (C=O), 1610, 1590 (C=C).

Calcd: C, 58.02; H, 5.31; N, 3.07%.

Found: C, 58.10; H, 5.09; N, 3.06%.

Step 3. Preparation of N-[[6-methoxy-5-(trifluoromethyl)-1-naphthalenyl]-carbonyl]-N-[(ethoxy)carbonyl]glycine The N-[[6-methoxy-5-(trifluoromethyl)-1-naphthalenyl]carbonyl]-N-[(ethoxy)carbonyl]glycine, 1,1-dimethylethyl ester (2.5 g, 5.5 mmol) was stirred at 20° C. in formic acid (30 mL), for 6 hours. Water (400 mL) was added, and the mixture was extracted with ether (300 mL). The ether layer was washed with water (100 mL) then back-extracted with saturated sodium bicarbonate (250 mL). The aqueous layer was separated and poured into 2 normal hydrochloric acid (80 mL), the aqueous solution was extracted with ether (300 mL), washed with brine (200 mL), filtered, and evaporated to yield a white syrup, which crystallized on trituration with methylene chloride-hexanes to yield the pure product (1.0 g, 35%), m.p. 86°–88.5° C.

NMR (CDCl$_3$): δ8.35 (d, 1H, ArH), 8.15 (d, 1H, ArH), 7.35–7.55 (m, 3H, ArH), 4.85 (s, 2H, NCH$_2$), 4.0 (s, 3H, OCH$_3$), 3.95 (q, 2H, CH$_2$CH$_3$), 0.65 (t, 3H, CH$_2$CH$_3$).

IR (KBr, cm$^{-1}$): 3400–3000 (COOH, broad), 1760, 1740, 1700 (C=O), 1620, 1590 (C=C)(C-H).

Calcd.: C, 54.14; H, 4.04; N, 3.51%.

Found: C, 54.70; H, 4.30; N, 3.39%.

EXAMPLE 2

N-[[6-Methoxy-5-(trifluoromethyl)-1-naphthalenyl]-carbonyl]-N-[(methoxy)carbonyl]glycine

[(I): R=OCH$_3$; R$^1$=OCH$_3$; R$^2$=CF$_3$; X=O]

Step 1. Preparation of N-[[6-methoxy-5-(trifluoromethyl)-1-naphthalenyl]-carbonyl]carbamic acid, methyl ester Dimethylformamide (1.0 mL, anhydrous) was added to a solution of 6-methoxy-5-(trifluoromethyl)-1-naphthalenecarboxylic acid (10.0 g, 37.0 mmol) in thionyl chloride (100 mL), then refluxed for 1 hour. The solution was cooled and the solvent was evaporated. The solvent was replaced with benzene (100 mL) and reevaporated to yield the acid chloride which was stirred in carbon tetrachloride (250 mL), and added to a suspension of silver cyanate (5.5 g, 37.0 mmol) in carbon tetrachloride (100 mL). The resultant mixture was refluxed for 16 hours, cooled to room temperature and the solvent was evaporated. The residue was stirred in benzene (250 mL) and a solution of methanol (25 mL, 0.616 mol) in benzene (100 mL) was added to it. This was stirred at 70° C. for 3 hours then filtered while hot. The filtrate was allowed to cool and crystallize. The crystals were then collected by suction filtration, washed with hexane and dried under vacuo to give the white solid product (1.3 g, 11%), m.p. 188°–190° C.

NMR (DMSO-d$_6$): δ10.2 (s, 1H, N-H), 8.20 (d, 1H, ArH), 8.10 (d, 1H, ArH), 7.70 (m, 2H, ArH), 7.46 (d, 1H, ArH), 4.0 (s, 3H, OCH$_3$), 3.40 (s, 3H, COOCH$_3$).

IR (KBr, cm$^{-1}$): 3400, 3200 (N-H), 1770, 1690 (C=O), 1615, 1600 (C=C).

Calcd.: C, 55.05; H, 3.70; N, 4.28%.

Found: C, 55.78; H, 3.98; N, 5.18%.

Step 2. Preparation of N-[[6-methoxy-5-(trifluoromethyl)-1-naphthalenyl]-carbonyl]-N-[(methoxy)carbonyl]glycine, 1,1-dimethylethyl ester N-[[6-Methoxy-5-(trifluoromethyl)-1-naphthalenyl]-carbonyl]carbamic acid, methyl ester (2.2 g, 6.72 mmol) was added to a suspension of sodium hydride (60% in oil, 0.29 g, 7.25 mmol) in tetrahydrofuran (anhydrous, 150 mL) and the mixture stirred for 1.5 hours at 20° C. tert-Butyl bromoacetate (1.20 mL, 7.40 mmol) was added and the resultant solution was stirred for 20 hours at 20° C. The solvent was evaporated and the residual solid triturated with hexanes (3×20 mL), to yield the pure product (2.1 g, 71.2%) as a white crystalline solid.

NMR (DMSO): δ8.20 (d, 1H, ArH), 8.10 (d, 1H, ArH), 7.64–7.70 (m, 2H, ArH), 7.40–7.60 (d, 1H, ArH), 4.60 (s, 2H, NCH$_2$), 4.0 (s, 3H, OCH$_3$), 3.42 (s, 3H, OCH$_3$), 1.42 (s, 9H, C(CH$_3$)$_3$).

IR (KBr, cm$^{-1}$): 3000 (C-H), 1770 (C=O), 1750 (C=O), 1690 (C=O), 1620, 1600 (C=C).

Calcd.: C, 57.40; H, 4.59; N, 3.19%.
Found: C, 56.68; H, 5.52; N, 4.67%.

Step 3. Preparation of N-[[6-methoxy-5-(trifluoromethyl)-1-naphthalenyl]-carbonyl]-N-[(methoxy)carbonyl]glycine Trifluoroacetic acid (20.0 mL, 260 mmol) was added to a solution of N-[[6-methoxy-5-(trifluoromethyl)-1-naphthalenyl]carbonyl]-N-(methoxycarbonyl)-glycine,1,1-dimethylethyl ester (1.5 g, 3.41 mmol) in chloroform (25 mL) at 20° C. and the mixture refluxed for 1.5 hours. The solution was cooled to 20° C. and the solvent evaporated under reduced pressure. The residual solid was recrystallized from acetone-water and dried at 70° C./0.1 m.m. Hg to yield the pure product as a white solid (1.4 g, 100%), m.p. 148°-150° C.

NMR (DMSO): δ9.82 (s, 1H, COOH), 8.20 (d, 1H, ArH), 8.10 (d, 1H, ArH), 7.64-7.70 (m, 2H, ArH), 7.50 (d, 1H, ArH), 4.60 (s, 2H, NCH$_2$), 4.05 (s, 3H, OCH$_3$), 3.42 (s, 3H, COOCH$_3$).

IR (KBr, cm$^{-1}$): 3300-3000 (COOH), 1775 (C=O), 1730, 1700 (C=O), 1620 (C=C).

Calcd.: C, 52.99; H, 3.66; N, 3.63%.
Found: C, 52.80; H, 3.47; N, 3.55%.

EXAMPLE 8

N-Formyl-N-[[6-methoxy-5-(trifluoromethyl)-1-naphthalenyl]carbonyl]glycine

[(I): R=H; R$^1$=OCH$_3$; R$^2$=CF$_3$; X=O]

Step 1. Preparation of 6-methoxy-5-(trifluoromethyl)-1-naphthalene-carboxamide

Dimethylformamide (0.05 mL) was added to a stirred suspension of 5-(trifluoromethyl)-6-methoxy-1-naphthalenecarboxylic acid (14.84 g, 54.32 mmol) in thionyl chloride (30 mL). A reflux condenser and CaCl$_2$ drying tube were attached to the apparatus and the reaction mixture was heated to 50°-60° C. Dissolution occurred within 10 minutes. After 20 minutes the reaction mixture was cooled to room temperature, and the excess SOCl$_2$ was removed. The residual solid was dissolved in dry THF (100 mL) and added dropwise over a 10-15 minute period to a cold (0°-10° C.) mechanically stirred solution of concentrated ammonium hydroxide (400 mL). After an additional 10 minutes, water (300 mL) was added and the reaction mixture was filtered. The white solid was washed with water and dried in vacuo (14.9 g), m.p. 258° C.

NMR (d$^6$DMSO, 200 MHz): δ4.00 (s, 3H, OCH$_3$), 7.5-7.8 (m, 4H, ArH and NH), 8.0-8.2 (m, 2H, ArH and NH), 8.54 (d, 1H, ArH).

IR (KBr, cm$^{-1}$): 3360, 3190 (NH), 1660 (C=O).

Calcd.: C, 58.00; H, 3.74; N, 5.20%.
Found: C, 58.31; H, 3.77; N, 5.08%.

Step 2. Preparation of N-formyl-6-methoxy-5-(trifluoromethyl)-1-naphthalenecarboxamide A suspension of 6-methoxy-5-(trifluoromethyl)-1-naphthalenecarboxamide (14.99 g, 55.7 mmole) in dimethylformamide dimethylacetal (22.2 mL, 3.0 eq) was heated to 120° C. under a dry nitrogen atmosphere for 5 minutes. The resultant solution was cooled to 0° C. in an ice bath where crystals formed. The crystals were collected by suction filtration then dissolved in acetic acid (70% by volume aqueous solution, 70 mL). After 5 minutes, a precipitate appeared. The precipitate was collected by suction filtration, washed with water (1×40 mL), and dried in vacuo to provide a white solid (14.95 g, 90%). A portion of this solid (1.5 g) was recrystallized in 1:2 hexane:chloroform to provide the product as white needles (0.939 g, 56%), m.p. 187°-189° C.

NMR (d$^6$DMSO, 400 MHz): δ4.02 (s, 3H, OCH$_3$), 7.71-7.78 (m, 3H, ArH), 8.24 (d, 1H, J=8.2 Hz, ArH), 8.54 (d, 1H, J=9.8 Hz, ArH), 9.26 (d, 1H, J=9.1 Hz, CHO), 11.81 (d, 1H, J=9.1 Hz, NH).

IR (KBr, cm$^{-1}$): 3300 (NH), 1732 (C=O), 1683 (C=O), 1620 and 1599 (C=C).

Calcd.: C, 56.57; H, 3.39; N, 4.71%.
Found: C, 56.58; H, 3.65; N, 4.65%.

Step 3. Preparation of N-formyl-N-[[6-methoxy-5-(trifluoromethyl)-1-naphthalenyl]carbonyl]glycine, 1,1-dimethylethyl ester Sodium hydride (60% by weight dispersion in mineral oil, 2.04 g, 1.10 eq) was added to a solution of N-formyl-6-methoxy-5-(trifluoromethyl)-1-naphthalenecarboxamide (13.80 g, 46.4 mmole) in anhydrous dimethylformamide (100 mL) at 0° C. under a dry nitrogen atmosphere. The reaction was warmed to room temperature for 15 minutes, then recooled to 0° C. t-Butylbromo acetate (7.49 mL, 1.0 eq) was added to the reaction mixture. After 65 minutes, more t-butylbromo acetate (1.50 mL, 0.2 eq) was added. After 1 1/4 hours, the reaction was quenched with saturated aqueous ammonium chloride (100 mL) and warmed to room temperature. The reaction mixture was diluted with water (1.5 L) and extracted with ether (3×250 mL). The ether extracts were combined, dried with magnesium sulfate, filtered, and the ether was removed. The crude product was purified by flash chromatography (17:3 petroleum ether:ethyl acetate, silica) to provide the product as white crystals (14.53 g, 76%), m.p. 101°-104° C.

NMR (CDCl$_3$, 400 MHz): δ4.02 (s, 3H, OCH$_3$), 4.59 (s, 2H, CH$_2$CO$_2$), 7.46 (d, 1H, J=9.4 Hz, ArH), 7.51 (d, 1H, J=7.0 Hz, ArH), 7.62 (t, 1H, J=7.1 Hz, ArH), 8.30 (d, 1H, J=9.4 Hz, ArH), 8.38 (d, 1H, J=8.9 Hz, ArH), 8.65 (s, 1H, CHO).

IR (KBr, cm$^{-1}$): 1758 (C=O), 1730 (C=O), 1673 (C=O), 1618 and 1599 (C=C).

Calcd.: C, 58.39; H, 4.90; N, 3.40%
Found: C, 58.69; H, 4.88; N, 3.32%.

Step 4. Preparation of N-formyl-N-[[6-methoxy-5-(trifluoromethyl)-1-naphthalenyl]carbonyl]glycine A solution of N-formyl-N-[[6-methoxy-5-(trifluoromethyl)-1-naphthalenyl]-carbonyl]glycine,1,1-dimethylethyl ester (12.86 g, 31.3 mmole) in trifluoroacetic acid (100 mL) was stirred at room temperature for 5 minutes. The reaction was diluted with water (700 mL) and the resultant precipitate was collected by suction filtration. The solid was washed with water (2×25 mL) and recrystallized in 2:1 hexane:chloroform to provide the product as white needles (5.09 g, 46%), m.p. 142°-144° C.

NMR (d$^6$DMSO, 400 MHz): δ4.02 (s, 3H, OCH$_3$), 4.53 (s, 2H, NCH$_2$CO$_2$H), 7.65 (d, 1H, J=6.9 Hz, ArH), 7.73-7.78 (m, 2H, ArH), 8.24-8.28 (m, 2H, ArH), 8.69 (s, 1H, CHO), 13.26 (broad peak, 1H, CO$_2$H).

IR (KBr cm$^{-1}$): 3140 (COOH), 1753 (C=O), 1702 (C=O), 1651 (C=O).

Calcd.: C, 54.09; H, 3.40; N, 3.94%.
Found: C, 54.29; H, 3.63; N, 3.83%.

EXAMPLE 10

N-Benzoyl-N-[[6-methoxy-5-(trifluoromethyl)-1-naphthalenyl]carbonyl]glycine

[(I): R=Ph; R$^1$=OCH$_3$; R$^2$=CF$_3$; X=O]

Step 1. Preparation of N-benzoyl-N-6-methoxy-5-(trifluoromethyl)-1-naphthalenecarboxamide According to the procedure of J. D. Albright et al, J. Med. Chem., 26, 1393 (1983), a solution of benzamide (9.96 g, 1.2 eq) in anhydrous tetrahydrofuran (175 mL) was added to a stirred suspension of sodium hydride (60% by weight dispersion in mineral oil, 3.29 g, 1.2 eq) in anhydrous THF (175 mL) at room temperature under a dry nitrogen atmosphere. After 20 minutes, a solution of 5-(trifluoromethyl)-6-methoxy-1-naphthalenecarboxylic acid chloride (~20.0 g, 68.5 mmole) in anhydrous THF (100 mL) was added slowly to the reaction mixture. [5-(Trifluoromethyl)-6-methoxy-1-naphthalenecarboxylic acid chloride was prepared from 5-(trifluoromethyl)-6-methoxy-1-naphthalenecarboxylic acid (18.50 g, 68.5 mmole), thionyl chloride (28 mL, 3.5 eq), and dimethylformamide (0.167 mL, 0.03 eq) in anhydrous tetrahydrofuran (56 mL). The solution was stirred at room temperature for 45 minutes, then the organic solvent was removed. The acid chloride was used without further purification.] After 50 minutes, the reaction mixture was diluted with water (1.3 L). The aqueous phase was acidified to pH5 with concentrated hydrochloric acid and extracted with ethyl acetate (8×300 mL). The extracts were combined, dried with magnesium sulfate, and the ethyl acetate was removed. The crude product was recrystallized in 1:4 chloroform:acetonitrile to provide the off white solid (6.96 g, 27%), m.p. 248°–250° C.

NMR (d$^6$DMSO, 200 MHz): δ4.01 (s, 3H, ArOCH$_3$), 7.51 (t, 2H, J=7.6 Hz, PhH), 7.59–7.71 (m, 4H, ArH and PhH), 7.94 (d, 2H, J=7.7 Hz, PhH), 8.18 (broad d, 1H, ArH), 8.37 (d, 1H, J=10.0 Hz, ArH).

IR (KBr cm$^{-1}$): 3220 (NH), 3125 (NH), 2960 (CH), 1703 (C=O), 1672 (C=O), 1612 (C=C).

Anal. Calcd.: C, 64.34; H, 3.78; N, 3.75%.

Found: C, 64.18; H, 4.19; N, 4.00%.

Step 2. Preparation of N-benzoyl-N-[[6-methoxy-5-(trifluoromethyl)-1-naphthalenyl]carbonyl]glycine, 1,1-dimethylethyl ester Sodium hydride (60% by weight dispersion in mineral oil, 0.818 g, 1.10 eq) was added to a stirred suspension of N-benzoyl-N-6-methoxy-5-(trifluoromethyl)-1-naphthalenecarboxamide (6.96 g, 18.6 mmole) in anhydrous dimethylformamide (80 mL) at 0° C. under a dry nitrogen atmosphere. The reaction mixture was warmed to room temperature for 15 minutes, then cooled to 0° C. and t-butyl bromoacetate (3.00 mL, 1.0 eq) was added. After another 15 minutes, the reaction was warmed to room temperature. More t-butyl bromoacetate (0.60 mL, 0.2 eq) was added after 2⅔ hours and again 4⅓ hours total reaction time. After 22 hours, the reaction mixture was diluted with water (1.3 L). The aqueous phase was basified to pH9 with 10% aqueous sodium solution hydroxide solution. The aqueous phase was extracted with ether (5×300 mL). The ether extracts were combined, washed with saturated aqueous sodium chloride solution (1×300 mL), dried with magnesium sulfate, and the ether was removed. The crude product was flash chromatographed (4:1 petroleum ether:ethyl acetate, silica) to provide the product as a white solid (6.07 g, 67%), m.p. 146°–147.5° C.

NMR (CDCl$_3$, 400 MHz): δ1.54 (s, 9H, C(CH$_3$)$_3$), 4.00 (s, 3H, ArOCH$_3$), 4.74 (broad s, 2H, NCH$_2$CO$_2$), 6.84 (t, 2H, J=7.8 Hz, PhH), 6.94 (t, 1H, J=7.4 Hz, PhH), 7.28–7.35 (m, 4H, ArH and PhH), 7.58 (d, 1H, J=7.1 Hz, ArH), 8.00 (d, 1H, J=9 Hz, ArH), 8.35 (d, 1H, J=9.6 Hz, ArH).

IR (neat, cm$^{-1}$): 2998 (CH), 1746 (C=O), 1700 (C=O), 1663 (C=O), 1622 and 1598 (C=C).

Anal. Calcd.: C, 64.06; H, 4.96; N, 2.87%.

Found: C, 63.86; H, 5.14; N, 2.96%.

Step 3. Preparation of N-benzoyl-N-[[6-methoxy-5-(trifluoromethyl)-1-naphthalenyl]carbonyl]glycine A solution of N-benzoyl-N-[[6-methoxy-5-(trifluoromethyl)-1-naphthalenyl]carbonyl]glycine, 1,1-dimethylethyl ester (6.03 g, 12.4 mmole) in trifluoroacetic acid (40 mL) was stirred at room temperature for 10 mintutes, then diluted with water (600 mL) and extracted with ether (2×300 mL). The extracts were combined, washed with saturated aqueous sodium chloride (1×100 mL), dried with magnesium sulfate, and the ether was removed. The resultant oil was suspended in water (300 mL) and the aqueous phase was slowly neutralized to pH5 with 10% aqueous sodium hydroxide solution. The precipitate was collected by suction filtration, washed with water (2×25 mL), dried and flash chromatographed (9:1 chloroform:acetonitrile, 5% phosphoric acid in methanol treated silica). The solid was then recrystallized in 2:1 benzene:hexane to provide the product as white crystals (1.83 g, 33%), m.p. 143°–145° C. (dec.).

NMR (d$^6$DMSO, 400 MHz): δ4.01 (s, 3H, ArOCH$_3$), 4.69 (broad, s, 2H, NCH$_2$CO$_2$H), 6.94 (t, 2H, J=7.5 Hz, PhH), 7.04 (t, 1H, J=6.9 Hz, PhH), 7.29 (d, 2H, J=7.6 Hz, PhH), 7.47 (t, 1H, J=7.5 Hz, ArH), 7.61 (d, 1h, J=7.0 Hz, ArH), 7.66 (d, 1H, J=9.6 Hz, ArH), 7.90 (broad d, 1H, J=8.7 Hz, ArH), 8.32 (d, 1H, J=9.6 Hz, ArH).

IR (KBr, cm$^{-1}$): 1721 (C=O), 1708 (C=O), 1669 (C=O), 1622 and 1602 (C=C).

Anal. Calcd.: C, 61.26; H, 3.74; N, 3.25%.

Found: C, 61.06; H, 4.01; N, 3.53%.

EXAMPLE 11

N-[(Dimethylamino)carbonyl]-N-[[6-methoxy-5-(trifluoromethyl)-1-naphthalenyl]carbonyl]glycine

[(I): R=N(CH$_3$)$_2$; R$^1$=OCH$_3$; R$^2$=CF$_3$; X=O]

Step 1. Preparation of N-[(dimethylamino)carbonyl]-6-methoxy-5-(trifluoromethyl)-1-naphthaenecarboxamide A suspension of 6-methoxy-5-(trifluoromethyl)-1-naphthalenecarboxamide (20.0 g, 74.29 mmol) in dry THF (400 mL) was added to a stirred suspension of sodium hydride (4.0 g, 1.12 eq of a 50% dispersion in mineral oil) in THF (200 mL) and the resulting suspension was stirred at room temperature under a dry nitrogen atmosphere for 45 minutes. A solution of N,N-dimethylcarbamoylchloride (6.8 mL, 1.0 eq) in dry THF (100 mL) was added dropwise over a 20 minute period. After an additional 45 minutes, saturated aqueous NH$_4$Cl (200 mL) was added. The reaction mixture was added to 350 mL of water, acidified with 10% aqueous HCl and filtered. The precipitate was placed in 2 L of water and basified with 10% aqueous NaOH. This was filtered to remove the starting material. The filtrate was acidified with 10% aqueous HCl and filtered. This solid was washed with water and dried in vacuo to provide a white solid product (12.90 g, 51%), m.p. 169°–170.5° C.

NMR (d⁶DMSO, 400 MHz): δ2.46 (broad s, 6H, N(CH₃)₂), 4.01 (s, 3H, OCH₃), 7.59 (d, 1H, ArH), 7.66 (d, 1H, ArH), 7.70 (d, 1H, ArH), 7.70 (d, 1H, ArH), 8.15 (d, 1H, ArH), 8.38 (d, 1H, ArH), 10.46 (s, 1H, NH).

IR (KBr, cm⁻¹): 3420, 3230 (NH), 1695, 1670 (C=O).

Anal. Calcd.: C, 56.47; H, 4.44; N, 8.23%.
Found: C, 56.14; H, 4.59; N, 8.25%.

Step 2. Preparation of N-[(dimethylamino)carbonyl]-N-[[6-methoxy-5-(trifluoromethyl)-1-naphthalenyl]carbonyl]glycine,1,1-dimethylethyl ester Sodium hydride (1.90 g, 1.1 eq 50% dispersion in mineral oil) was added to a stirred, cold (0°–10° C.) solution of N-[(dimethylamino)carbonyl]-6-methoxy-5-(trifluoromethyl)-1-naphthalenecarboxamide (11.9 g, 34.97 mmol) in dry DMF (65 mL). The solution was allowed to warm to room temperature for 20 minutes and was then recooled to 0°–10° C. t-Butyl bromoacetate (6.7 mL, 1.15 eq) was added and the reaction mixture was warmed to room temperature. After 45 minutes the reaction mixture was added to water (1 L) and the water was basified (with 10% NaOH) and extracted with ether (7×400 mL). The ether was washed with saturated aqueous NaCl (700 mL) and dried (MgSO₄). The ether was removed to provide a white solid (12.2 g, 81%). A portion (2 g) was recrystallized from hexane to give a solid m.p. 117°–120° C.

NMR (d⁶DMSO, 400 MHz): δ1.46 (broad s, 9H, —C(CH₃)₃), 2.61 (broad s, 6H, N(CH₃)₂), 4.01 (s, 3H, OCH₃), 4.33 (braod s, 2H, N-CH₂-), 7.48 (m, 1H, ArH), 7.66 (t, 1H, ArH), 7.73 (d, 1H, ArH), 8.16 (d, 1H, ArH), 8.34 (m, 1H, ArH).

IR (KBr, cm⁻¹): 1730, 1685, 1650 (CONCO, CO₂H).
Anal. Calcd.: C, 58.15; H, 5.54; N, 6.16%.
Found: C, 58.26; H, 5.66; N, 6.24%.

Step 3. Preparation of N-[(dimethylamino)carbonyl]-N-[[6-methoxy-5-(trifluoromethyl)-1-naphthalenyl]carbonyl]glycine Trimethylsilyliodide (17.6 mL, 5.3 eq) was added to a stirred solution of the ester (10.0 g, 23.23 mmol) in CCl₄ (130 mL) at room temperature under a dry N₂ atmosphere. After 2.5 hours the CCl₄ was removed and water (500 mL) was added. The reaction mixture was acidified with 10% aq HCl and extracted with ethyl acetate (1×500 mL). The ethyl acetate extract was washed with dilute aqueous NaHSO₃ and dried (MgSO₄). The solvent was removed and the semisolid was triturated with 2:1 benzene:hexane (450 mL) and then filtered. The solid was triturated twice more with benzene (100 mL) and filtered. The white solid was dried in vacuo (7.15 g, 77%), m.p. 145°–147° C.

NMR (d⁶DMSO, 400 MHz): δ2.62 (broad s, 6H, N(CH₃)₂), 4.02 (s, 3H, OCH₃), 4.37 (broad s, 2H, N-CH₂-), 7.49 (m, 1H, ArH), 7.66 (t, 1H, ArH), 7.72 (d, 1H, ArH), 8.16 (m, 1H, ArH), 8.39 (m, 1H, ArH), 11.1 (m, 1H, OH).

IR (KBr, cm⁻¹): 3650–2350 (CO₂H), 1750, 1690, 1650 (CONCO, CO₂H).
MS (m/e): 398 (3%), 309 (4%), 253 (100%).
Anal. Calcd.: C, 54.27; H, 4.30; N, 7.03%.
Found: C, 54.23; H, 4.49; N, 7.22%.

EXAMPLE 18

N-[[6-Methoxy-5-(trifluoromethyl)-1-naphthalenyl]thioxmethyl]-N-[(methoxy)carbonyl]glycine

[(I): R=OCH₃; R¹=OCH₃; R²=CF₃; X=S]

Step 1. Preparation of N-[[6-methoxy-5-(trifluoromethyl)-1-naphthalenyl]-thioxmethyl]glycine,1,1-dimethylethyl ester N-[[6Methoxy-5-(trifluoromethyl)-1-naphthalenyl]-carbonyl]glycine,1,1-dimethylethyl ester, prepared by the process of Example 1, Step 1, (9.0 g, 23.4 mmol) was stirred in toluene (180 mL) at 20° C. Lawesson's Reagent, [2,4-bis(4-methoxyphenyl)-1,3-dithia-2,4-diphosphetane-2,4-disulfide](6.93 g, 34.2 mmol) was added, and the mixture stirred at 20° C. for 16 hours, then at 60° C. for 4 hours. The mixture was cooled to 20° C., ethyl acetate (450 mL), and water (500 mL) were added. The organic layer was separated, washed with brine (300 mL), dried (MgSO₄), filtered, and evaporated to yield the crude product which was chromatographed on silica/5:1 hexanes:ethyl acetate to yield the product which on trituration with hexanes yielded analytically pure material as a white solid (7.0 g, 74.6%), m.p. 145°–146° C.

NMR (DMSO-d₆): δ11.0 (s, 1H, NH), 8.50 (d, 1H, ArH), 8.10 (d, 1H, ArH), 7.60–7.80 (m, 2H, ArH), 7.40 (d, 1H, ArH), 4.40 (d, 2H, CH₂), 4.0 (s, 3H, OCH₃), 1.50 (s, 9H, C(CH₃)₃).

IR (KBr, cm⁻¹): 3310 (NH), 3000 (C-H), 1760, 1740 (C=O), 1620, 1600 (C=).
Calcd.: C, 57.13; H, 5.05; N, 3.51%.
Found: C, 57.35; H, 5.23; N, 3.59%.

Step 2. Preparation of N-[[6-methoxy-5-(trifluoromethyl)-1-naphthalenyl]-thioxmethyl]-N-(methoxycarbonyl)glycine,1,1-dimethylethyl ester Solid sodium hydroxide (powdered, 0.70 g, 17.5 mmol) was added to a solution of N-[[6-methoxy-5-(trifluoromethyl)-1-naphthalenyl]thioxmethyl]-glycine,1,1-dimethylethyl ester (4.0 g, 10.0 mmol) in dry acetone (200 mL) at −40° C. over a dry ice-acetonitrile bath and the mixture was stirred at −40° C. for 30 minutes. Methyl chloroformate (0.80 mL, 10.9 mmol) was added, and the mixture allowed to warm to 20° C. over a 2 hour period, then stirred at 20° C. for an additional hour. The solvent was evaporated and water (200 mL) added to the solid residue. The precipitated yellow solid was filtered, washed with water (3×100 mL), and petroleum ether (2×50 ml) to yield the product (3.6 g, 78.9%), m.p. 114°–117° C.

NMR (CDCl₃): δ8.35 (d, 1h, ArH), 8.15 (d, 1H, ArH), 7.25–7.50 (m, 3H, ArH), 5.10 (s, 2H, NCH₂), 4.0 (s, 3H, OCH₃), 3.40 (s, 3H, COOCH₃), 1.50 (s, 9H, C(CH₃)₃).

IR (KBr, cm⁻¹): 3310 (N-H), 3000 (C-H), 1760, 1740 (C=O), 1620, 1590 (C=C).
Calcd.: C, 55.14; H, 4.85; N, 3.06%.
Found: C, 58.06; H, 5.23; N, 3.24%.

Step 3. Preparation of N-[[6-methoxy-5-(trifluoromethyl)-1-naphthalenyl]-thioxomethyl]-N-(methoxycarbonyl)glycine Trifluoroacetic acid (5.0 ml, 64.9 mmol) was added to a solution of N-[[6-methoxy-5-(trifluoromethyl)-1-naphthalenyl]thioxomethyl-N-(methoxycarbonyl)-glycine,1,1-dimethylethyl ester (3.0 g, 6.5 mmol) in chloroform (25 ml) then stirred at 20° C. for 6 hours. Chloroform (50 mL), and water (150 mL), were added and the organic layer was separated, washed with brine (200 mL), dried (MgSO$_4$), filtered, and evaporated to yield an oil, which was extracted with aqueous saturated sodium bicarbonate solution (200 mL), washed with ether (200 mL), and poured into 2 normal hydrochloric acid (80 mL). The aqueous solution was extracted with ether (200 mL), washed with brine (3×100 mL), dried (MgSO$_4$), filtered, and evaporated to yield an oil which crystallized on trituration with chloroform-petroleum ether. The solid was recrystallized from chloroform-petroleum ether, and again from ethyl acetate-hexanes to yield the pure product as a white solid (1.58 g, 65%), m.p. 160° C.

NMR (DMSO-d$_6$): δ8.35 (d, 1H, ArH), 8.15 (d, 1H, ArH), 7.25–7.50 (m, 3H, ArH), 5.36 (s, 2H, NCH$_2$), 4.0 (s, 3H, OCH$_3$), 3.40 (s, 3H, COOCH$_3$).

IR (KBr, cm$^{-1}$): (3500–3400) COOH (broad), 1770, 1720 (C=O), 1620, 1590 (C=C).

Calcd.: C, 50.87; H, 3.52; N, 3.49%.
Found: C, 51.11; H, 3.91; H, 3.87%.

We claim:

1. The chemical intermediate compounds of formula (VII)

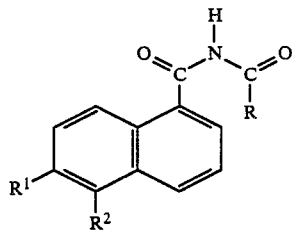

wherein R is hydrogen, lower alkyl containing 1 to 3 carbon atoms, lower alkoxy containing 1 to 6 carbon atoms, trifluoroethoxy, phenyl, benzyloxy, chloro- and nitro-substituted benzyloxy, or lower dialkylamino containing 1 to 3 carbon atoms; R$^1$ is hydrogen or lower alkoxy containing 1 to 3 carbon atoms and R$^2$ is halogen or lower perfluoroalkyl containing 1 to 3 carbon atoms.

* * * * *